(12) United States Patent
Yamaguchi

(10) Patent No.: US 12,193,955 B2
(45) Date of Patent: Jan. 14, 2025

(54) BRANCHED STENT GRAFTS AND STENT GRAFT DELIVERY SYSTEM AND METHODS

(71) Applicant: Dean Jared Yamaguchi, Winterville, NC (US)

(72) Inventor: Dean Jared Yamaguchi, Winterville, NC (US)

(*) Notice: Subject to any disclaimer, the term of this patent is extended or adjusted under 35 U.S.C. 154(b) by 0 days.

(21) Appl. No.: 17/712,604

(22) Filed: Apr. 4, 2022

(65) Prior Publication Data

US 2022/0218504 A1     Jul. 14, 2022

Related U.S. Application Data

(62) Division of application No. 15/146,982, filed on May 5, 2016, now abandoned.

(60) Provisional application No. 62/158,796, filed on May 8, 2015.

(51) Int. Cl.
| | |
|---|---|
| *A61F 2/954* | (2013.01) |
| *A61F 2/07* | (2013.01) |
| *A61F 2/06* | (2013.01) |
| *A61F 2/856* | (2013.01) |
| *A61F 2/89* | (2013.01) |

(52) U.S. Cl.
CPC ............... *A61F 2/954* (2013.01); *A61F 2/07* (2013.01); *A61F 2002/065* (2013.01); *A61F 2002/067* (2013.01); *A61F 2/856* (2013.01); *A61F 2/89* (2013.01); *A61F 2230/0067* (2013.01); *A61F 2230/0069* (2013.01); *A61F 2250/0039* (2013.01)

(58) Field of Classification Search
CPC ..................... A61F 2/954; A61F 2/856; A61F 2230/0069
See application file for complete search history.

(56) References Cited

U.S. PATENT DOCUMENTS

| | | | | |
|---|---|---|---|---|
| 6,030,414 A | * | 2/2000 | Taheri | A61F 2/856 623/1.1 |
| 6,524,335 B1 | * | 2/2003 | Hartley | A61F 2/07 623/1.13 |
| 6,645,242 B1 | * | 11/2003 | Quinn | A61F 2/07 623/1.13 |
| 6,706,062 B2 | * | 3/2004 | Vardi | A61F 2/82 623/1.35 |

(Continued)

*Primary Examiner* — Phong Son H Dang
(74) *Attorney, Agent, or Firm* — E. Eric Mills; Nicholas P. Stadnyk; Maynard Nexsen PC

(57) ABSTRACT

Branched stent grafts and a stent graft delivery system for, and methods of, endovascular repair of abdominal and/or thoracic aortic aneurysms are disclosed. Embodiments of the branched stent grafts include, but are not limited to, branched aorto-uni-iliac (AUI) stent grafts, branched bifurcated stent grafts, and branched thoracic stent grafts. In some embodiments, the branched stent grafts comprise one or more retrograde internal branches. In other embodiments, the branched stent grafts comprise one or more external branches. The stent graft delivery system comprises a larger directional sheath for positioning the branched stent grafts and one or more smaller sheaths for the delivery of, for example, covered stents for the complete exclusion of juxtarenal/pararenal abdominal aortic aneurysms. Methods of using the stent graft delivery system to deploy the branched stent grafts are provided.

13 Claims, 16 Drawing Sheets

(56) References Cited

U.S. PATENT DOCUMENTS

| | | | |
|---|---|---|---|
| 2003/0135257 A1* | 7/2003 | Taheri | A61B 17/12172 606/108 |
| 2003/0199967 A1 | 10/2003 | Hartley | |
| 2008/0097578 A1* | 4/2008 | Erickson | A61F 2/07 623/1.16 |
| 2010/0063576 A1* | 3/2010 | Schaeffer | A61F 2/07 623/1.13 |
| 2010/0268327 A1* | 10/2010 | Bruszewski | A61F 2/07 623/1.35 |
| 2012/0197383 A1* | 8/2012 | Ivancev | A61F 2/07 623/1.13 |
| 2012/0221096 A1* | 8/2012 | Roeder | A61F 2/07 623/1.13 |
| 2013/0013053 A1* | 1/2013 | Hartley | A61F 2/06 623/1.13 |
| 2013/0046371 A1* | 2/2013 | Greenberg | A61F 2/06 623/1.11 |
| 2013/0116775 A1 | 5/2013 | Roeder | |
| 2013/0131777 A1 | 5/2013 | Hartley | |
| 2013/0211505 A1* | 8/2013 | Robison | A61F 2/856 623/1.35 |
| 2014/0277335 A1* | 9/2014 | Greenberg | A61F 2/07 623/1.13 |
| 2015/0073534 A1* | 3/2015 | Roeder | A61F 2/856 623/1.35 |
| 2016/0302950 A1* | 10/2016 | Marmur | A61F 2/07 |
| 2017/0273809 A1* | 9/2017 | Marmur | A61F 2/07 |
| 2017/0333235 A1* | 11/2017 | Hartley | A61F 2/954 |
| 2018/0021157 A1* | 1/2018 | Marmur | A61F 2/9662 623/1.12 |

* cited by examiner

BRANCHED STENT GRAFTS AND STENT GRAFT DELIVERY SYSTEM AND METHODS

CROSS REFERENCE TO RELATED APPLICATIONS

This patent application is a divisional and claims priority to U.S. patent application Ser. No. 15/146,982 entitled "Branched Stent Grafts and Stent Graft Delivery System and Method" filed on May 5, 2016 which is related and claims priority to U.S. Provisional Application Ser. No. 62/158,796 filed on May 8, 2015; the entire disclosures of which are specifically incorporated by reference herein in their entirety as if made a part of the present disclosure.

TECHNICAL FIELD

The presently disclosed subject matter relates generally to stent graft systems and more particularly to branched stent grafts and a stent graft delivery system for, and methods of, endovascular repair of aortic aneurysms, including abdominal and thoracic aortic aneurysms.

BACKGROUND

Paravisceral abdominal aortic aneurysms are complex aneurysms. Successful exclusion of paravisceral abdominal aortic aneurysms, in large part, hinges upon the ability to cannulate the visceral vessels through the main body of the device and then to deliver covered stents bridging the renal or mesenteric vessel to the stent graft. Currently, there is one Food and Drug Administration (FDA)-approved fenestrated aortic stent graft system marketed in the United States for the treatment of paravisceral abdominal aortic aneurysms. This device is custom-built for each patient based on pre-operative computed tomographic studies and often takes at least three weeks to construct. Consequently, the one FDA-approved fenestrated aortic stent graft system is costly and requires a certain amount of advance planning and work.

Further, anatomic features, as well as design constraints of the stent grafts themselves (e.g., not placing fenestrations across device struts), limit the surgeon's capability to accurately deliver these devices. There are approaches using off-the-shelf devices for the treatment of juxtarenal/pararenal/paravisceral abdominal aortic aneurysms. However, these approaches are considered off-label and not according to the "Instructions for Use" by the various stent graft manufacturers.

SUMMARY

An aspect of the present disclosure is directed to an endovascular repair device comprising a stent graft comprising a main body section, with the main body section having an outer wall, and with said outer wall having at least one fenestration; and at least one branch in fixed communication with the fenestration, with said branch configured to extend a predetermined distance from the main body section, said branch having a proximate end and a distal end, said proximal end in communication with the fenestration.

In a further aspect, the main body is substantially cylindrical and substantially hollow.

In yet another aspect the stent graft is a branched stent graft.

In a still further aspect, the stent graft is a branched bifurcated stent graft.

In a further aspect, the stent graft is a covered stent graft.

In yet another aspect, the branch is substantially frusto-conical in shape, with the proximal end having a proximal end opening diameter that is greater than a distal end opening diameter.

In another aspect, the branch extends inward from the outer wall of the main body and into the main body for a predetermined distance.

In yet another aspect, the branch extends outward from the outer wall of the main body and outside of the main body for a predetermined distance.

In another aspect, the branch substantially conforms to the main body profile.

In still another aspect, the device further comprises at least one secondary stent graft dimensioned to pass into the fenestration and into the branch that is in fixed communication with the fenestration.

In yet another aspect, the device is configured to be implanted in a body as an abdominal or a thoracic stent graft.

In another aspect, the present disclosure is directed to a kit comprising a stent graft comprising a main body section, with the main body section having an outer wall, and with the outer wall having at least one fenestration and at least one branch in communication with the fenestration, and with the branch configured to extend a predetermined distance from the main body section, with the branch having a proximate end and a distal end, and with the proximal end in communication with the fenestration; a primary stent graft sheath configured to accommodate a primary guide wire passing through the primary stent graft sheath; and at least one secondary stent graft sheath configured to accommodate at least one secondary guide wire passing through said secondary stent graft sheath.

A further aspect of the present disclosure is directed to a method for deploying a stent graft into a body comprising introducing a stent graft into a body, with the stent graft comprising a main body section, and with the main body section having an outer wall, with the outer wall having at least one fenestration and at least one branch in communication with the fenestration, with the branch configured to extend a predetermined distance from the main body section, and with the branch having a proximate end and a distal end, with the proximal end in communication with the fenestration.

BRIEF DESCRIPTION OF THE DRAWINGS

Figure 1:
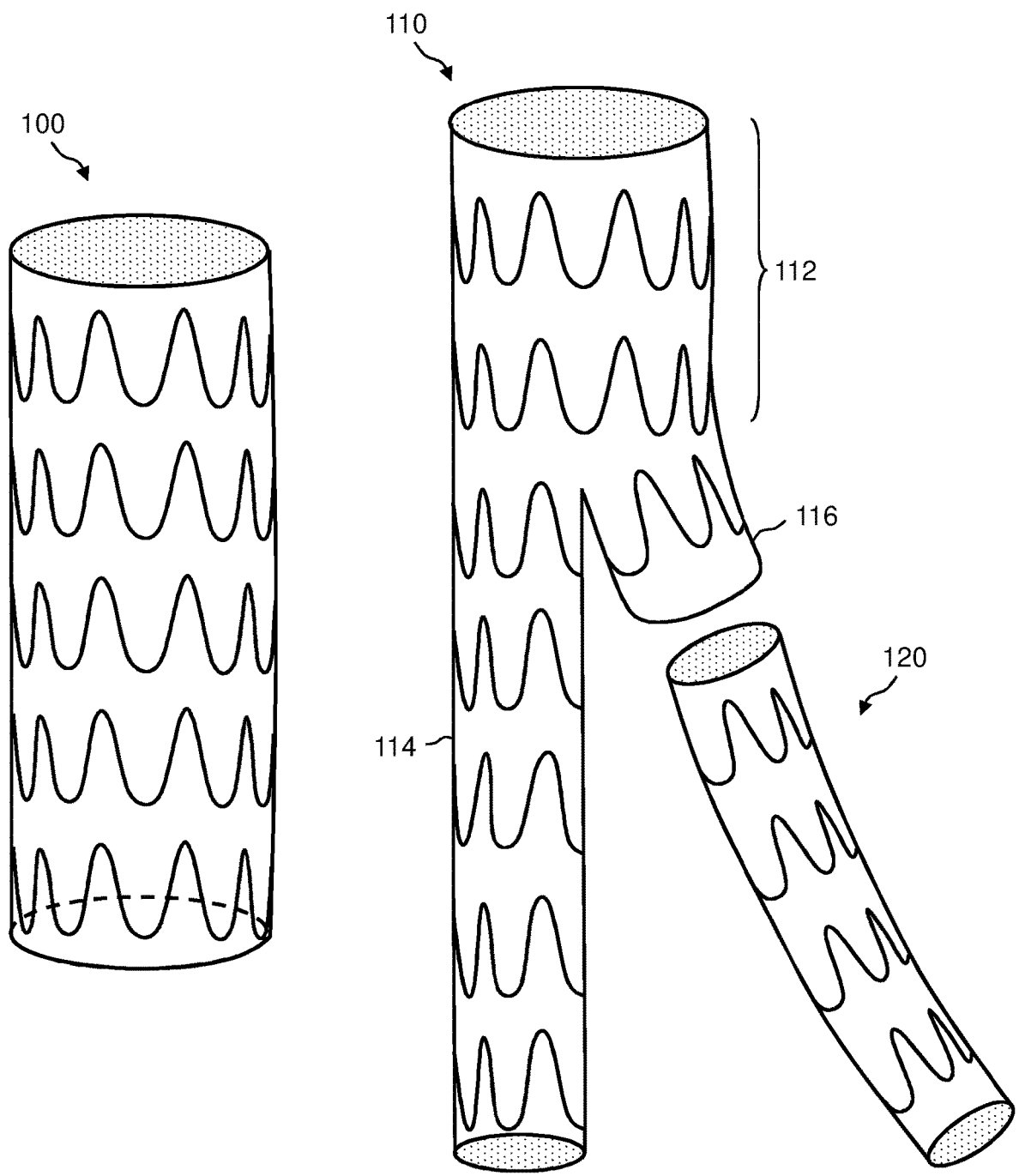
Figure 2:
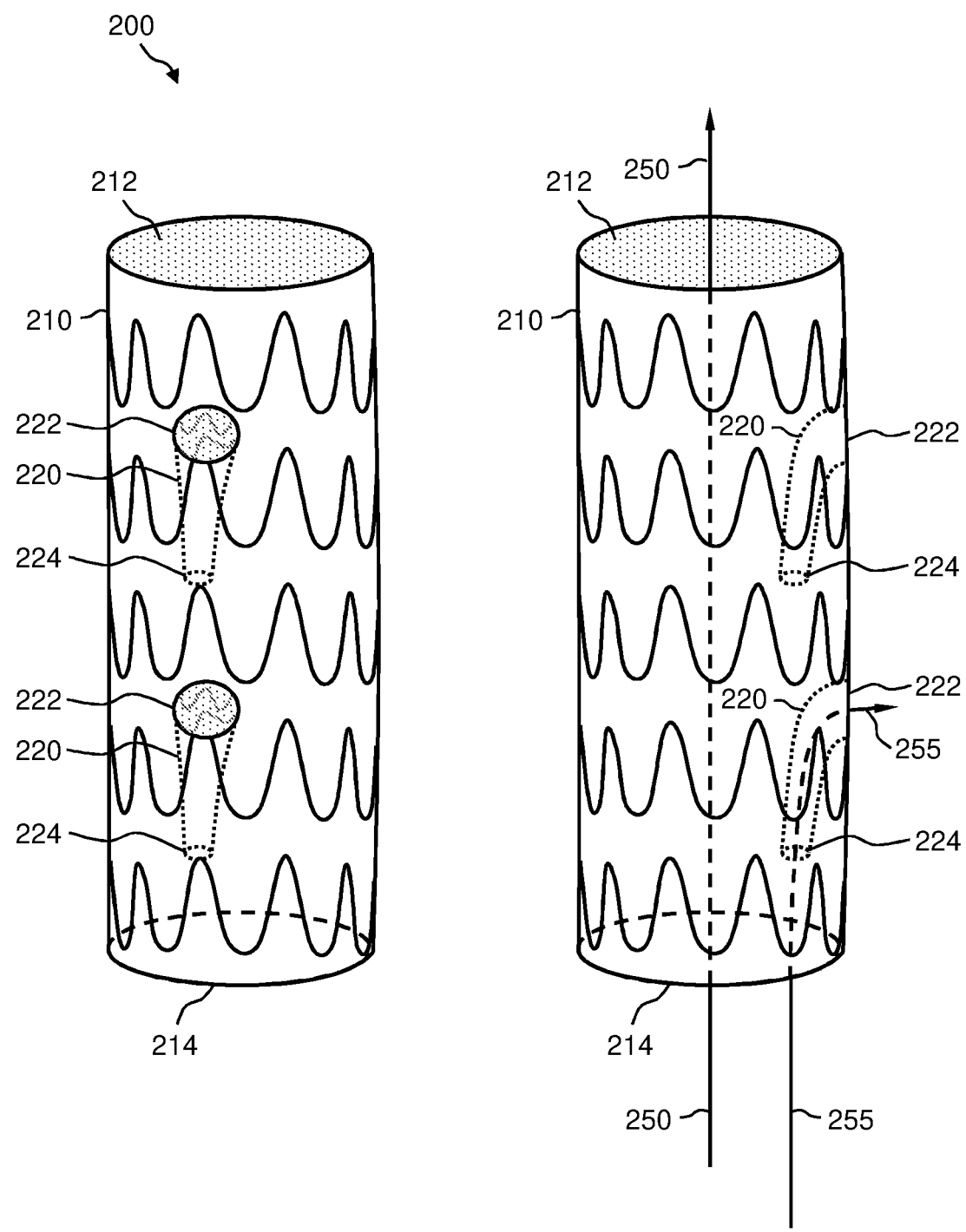
Figure 3:
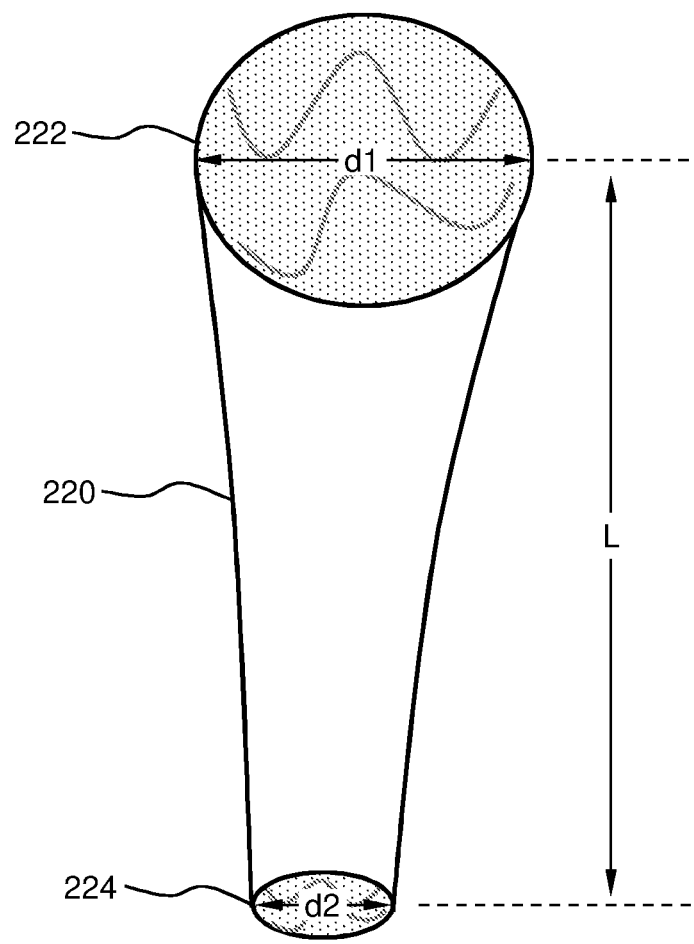
Figure 4:
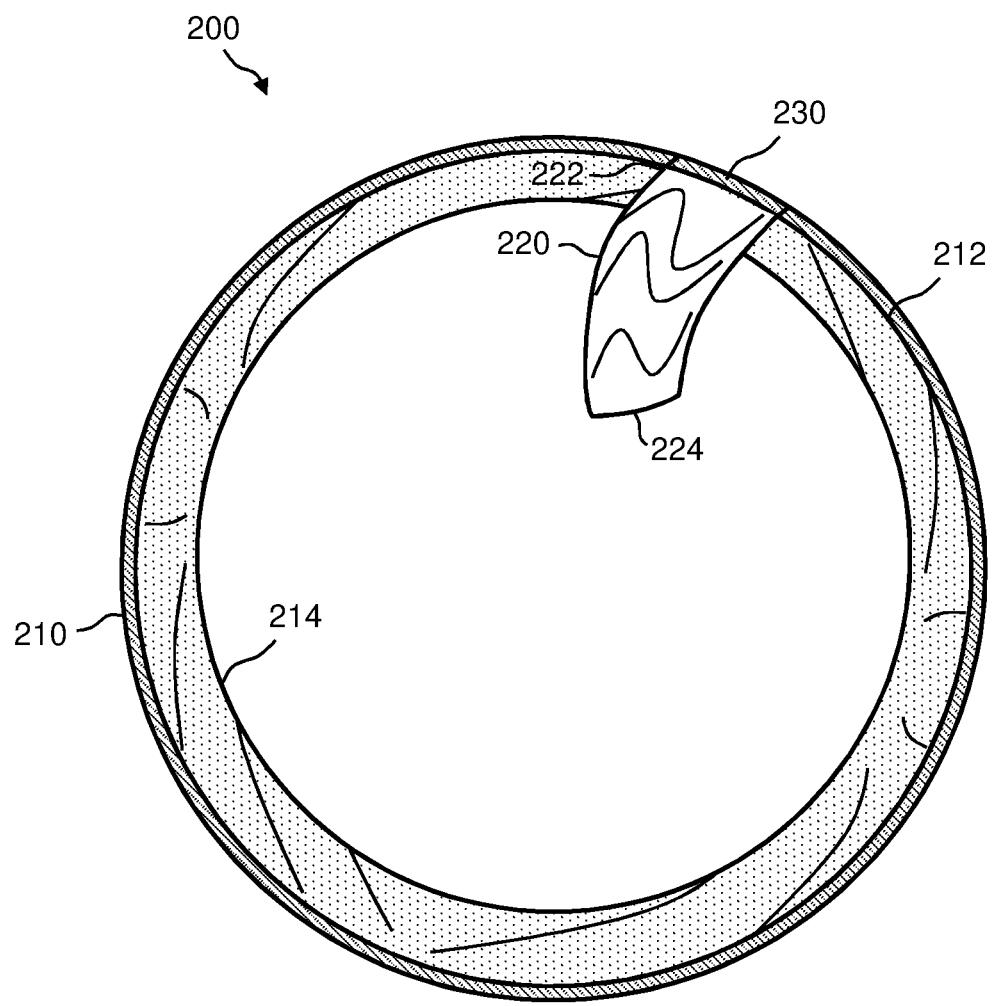
Figure 5:
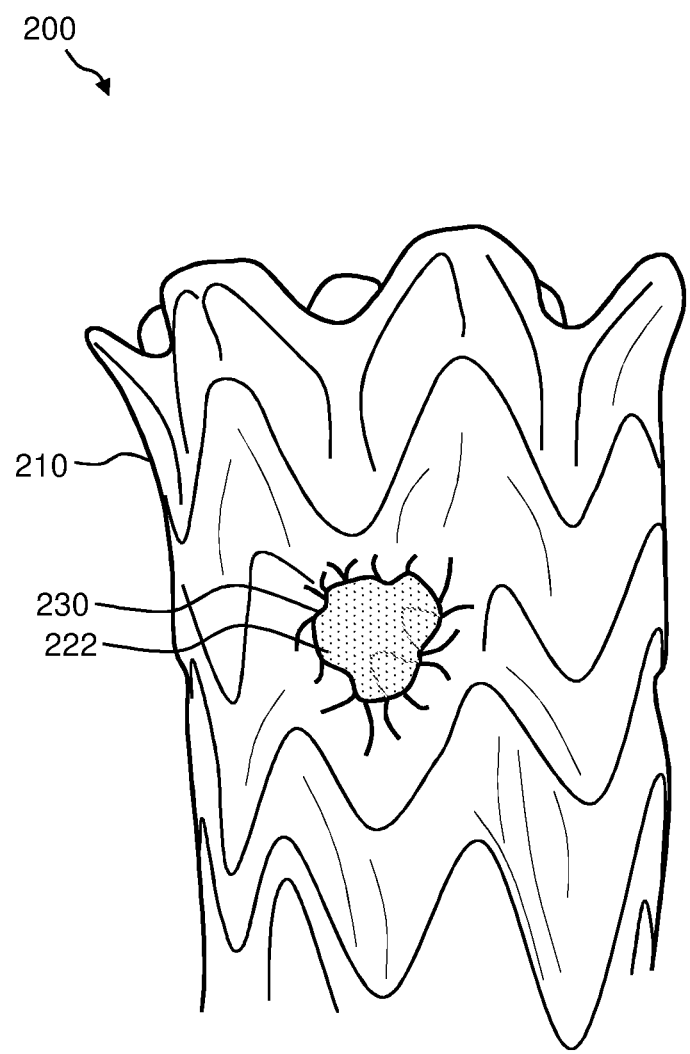
Figure 6:
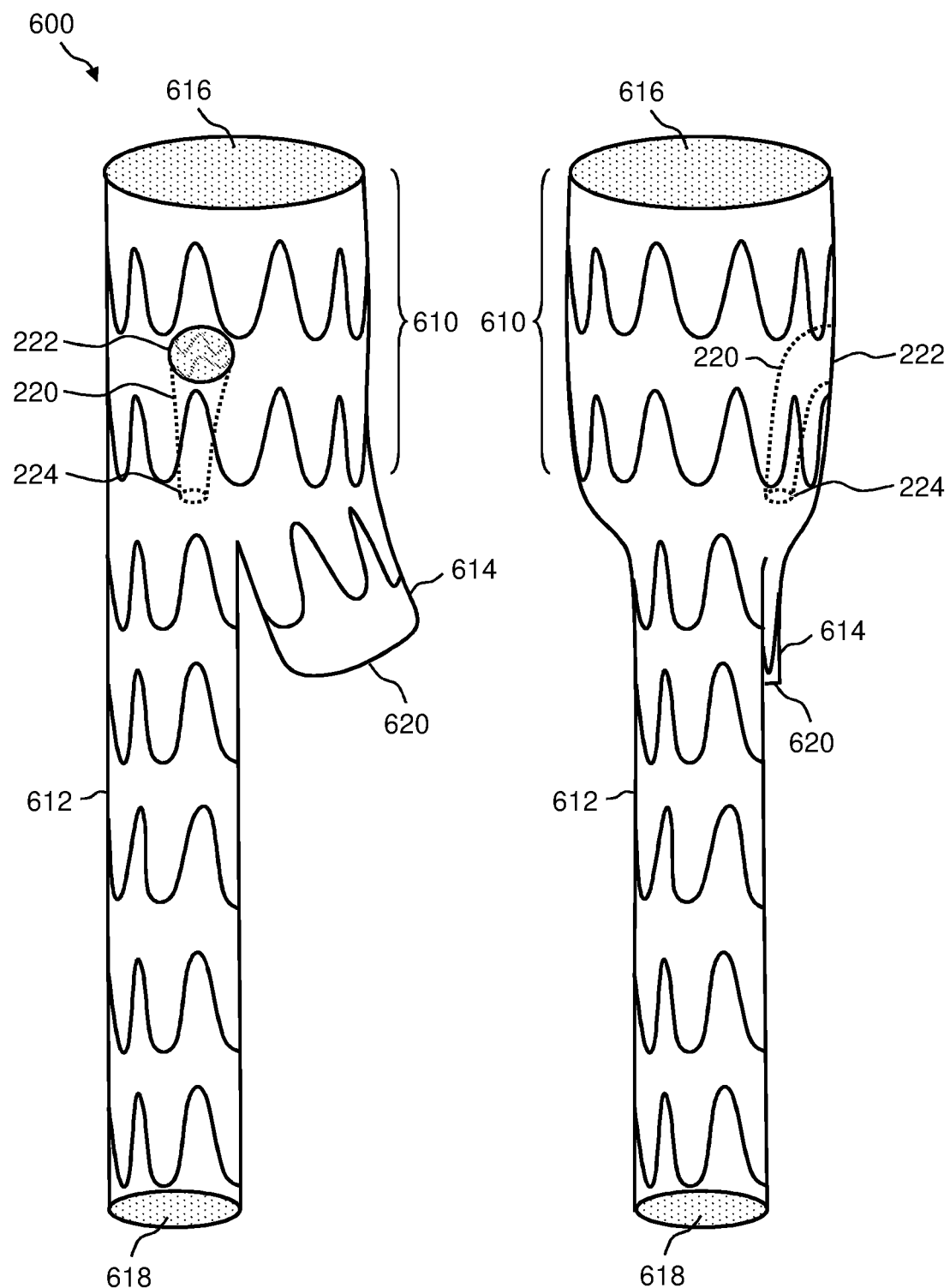
Figure 7:
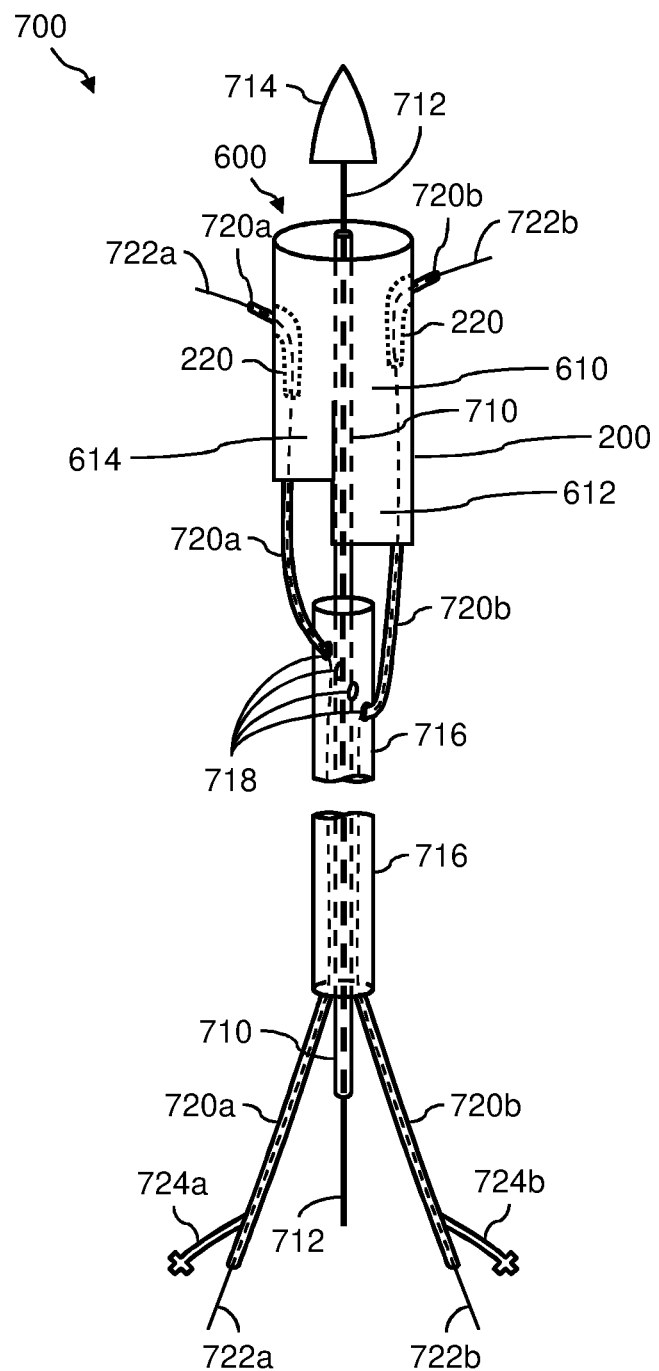
Figure 8:
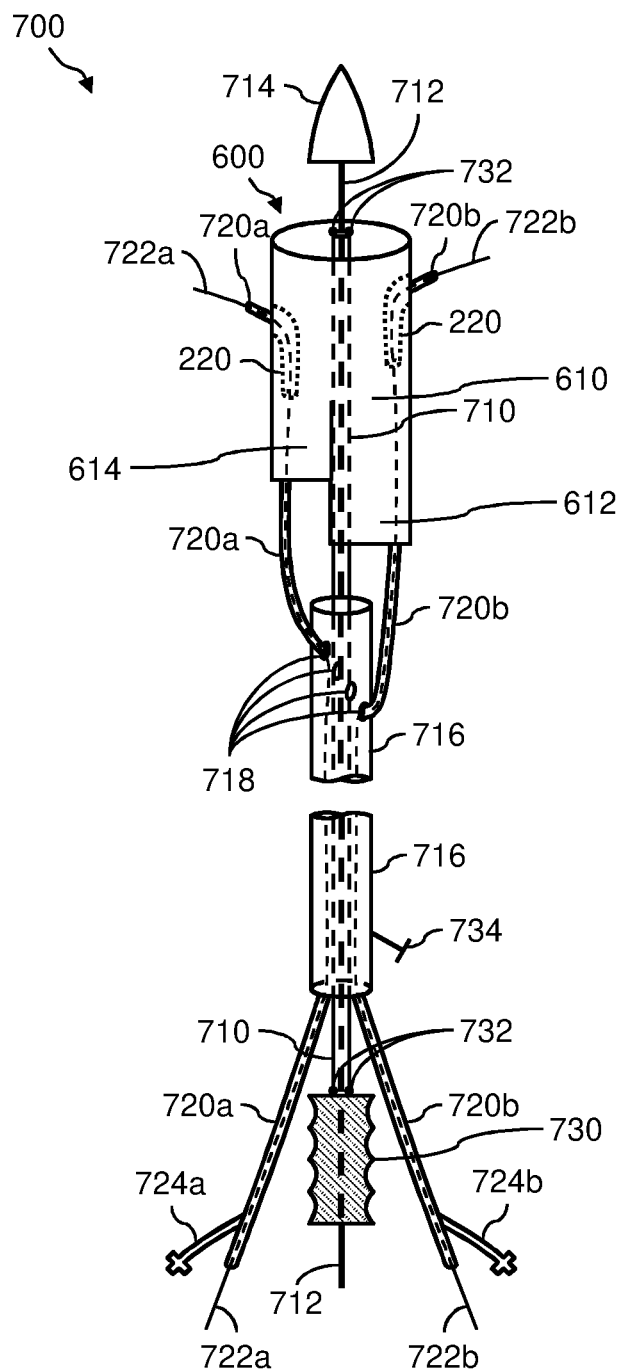
Figure 9:
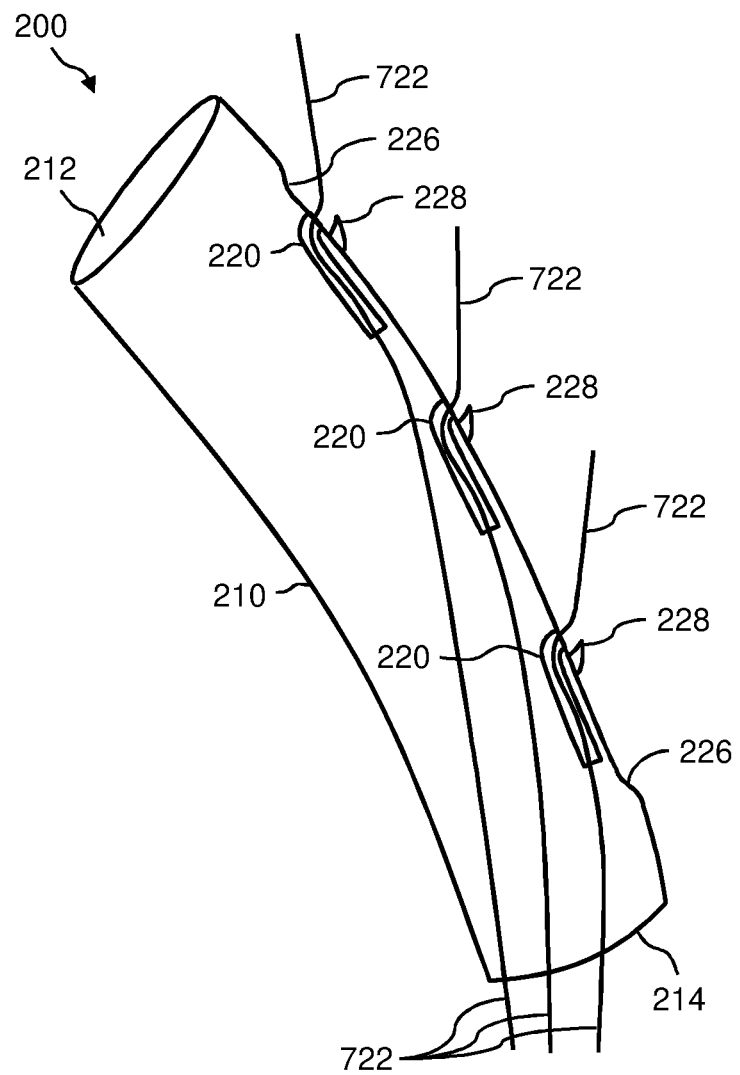
Figure 10:
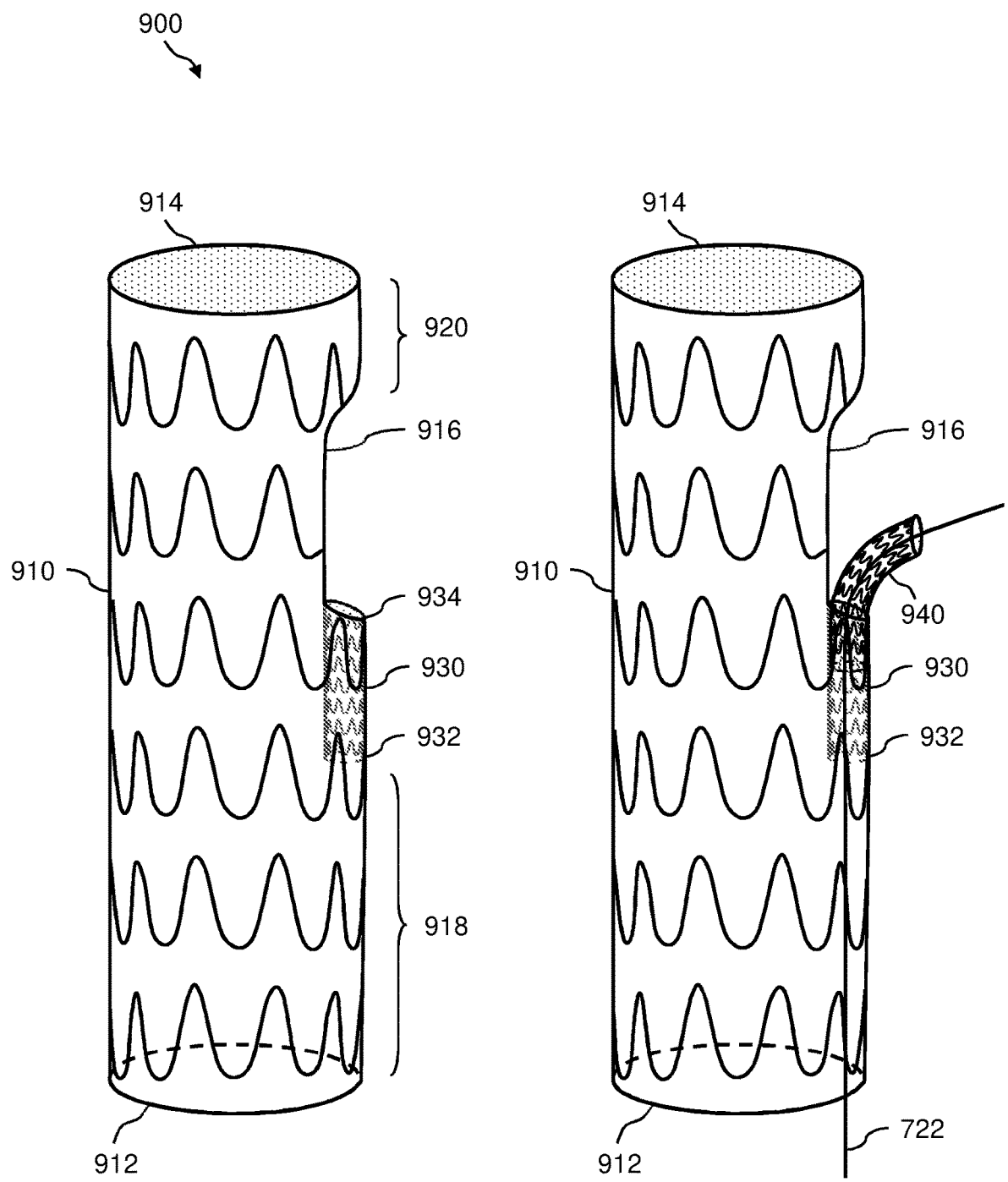
Figure 11:
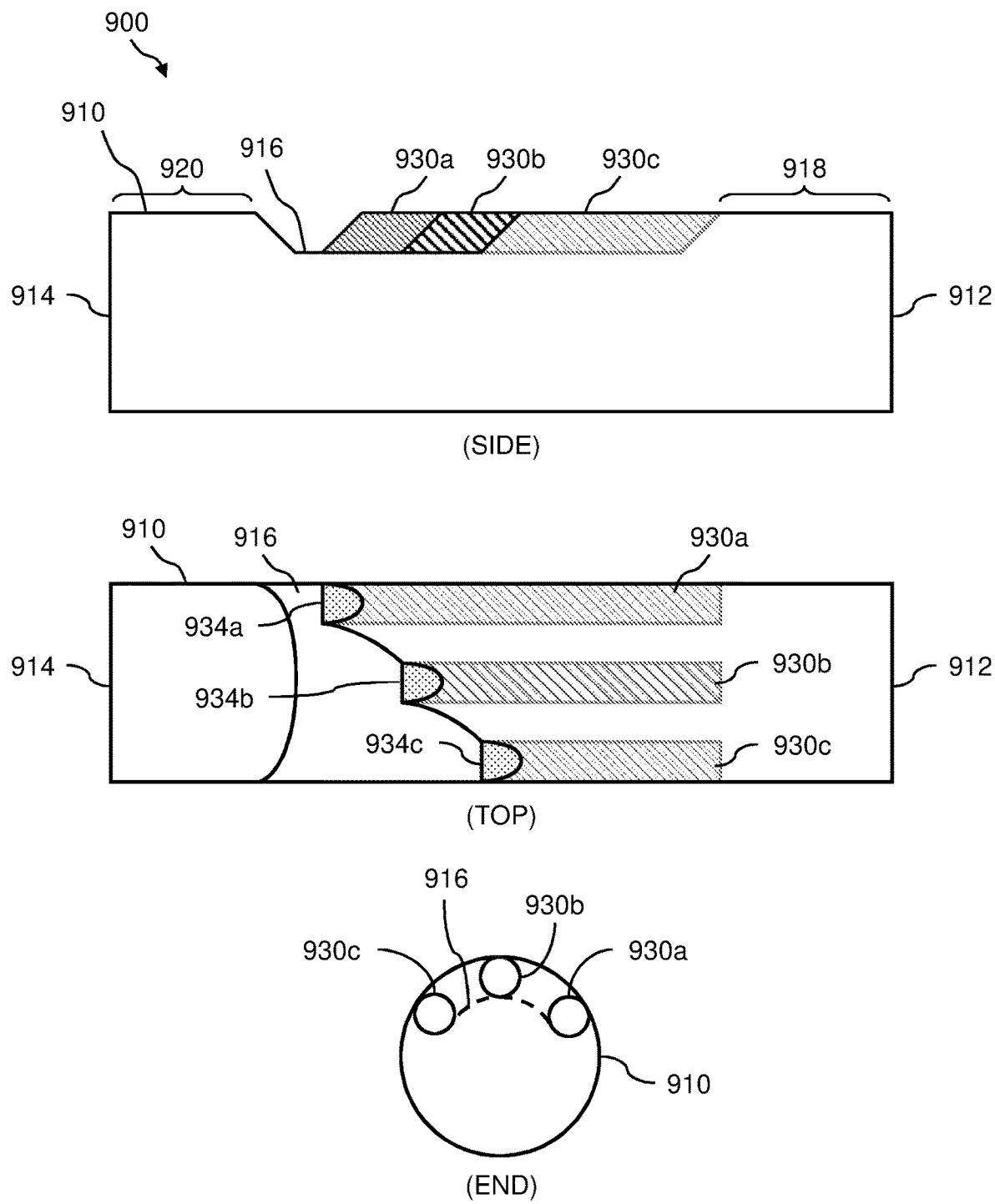
Figure 12:
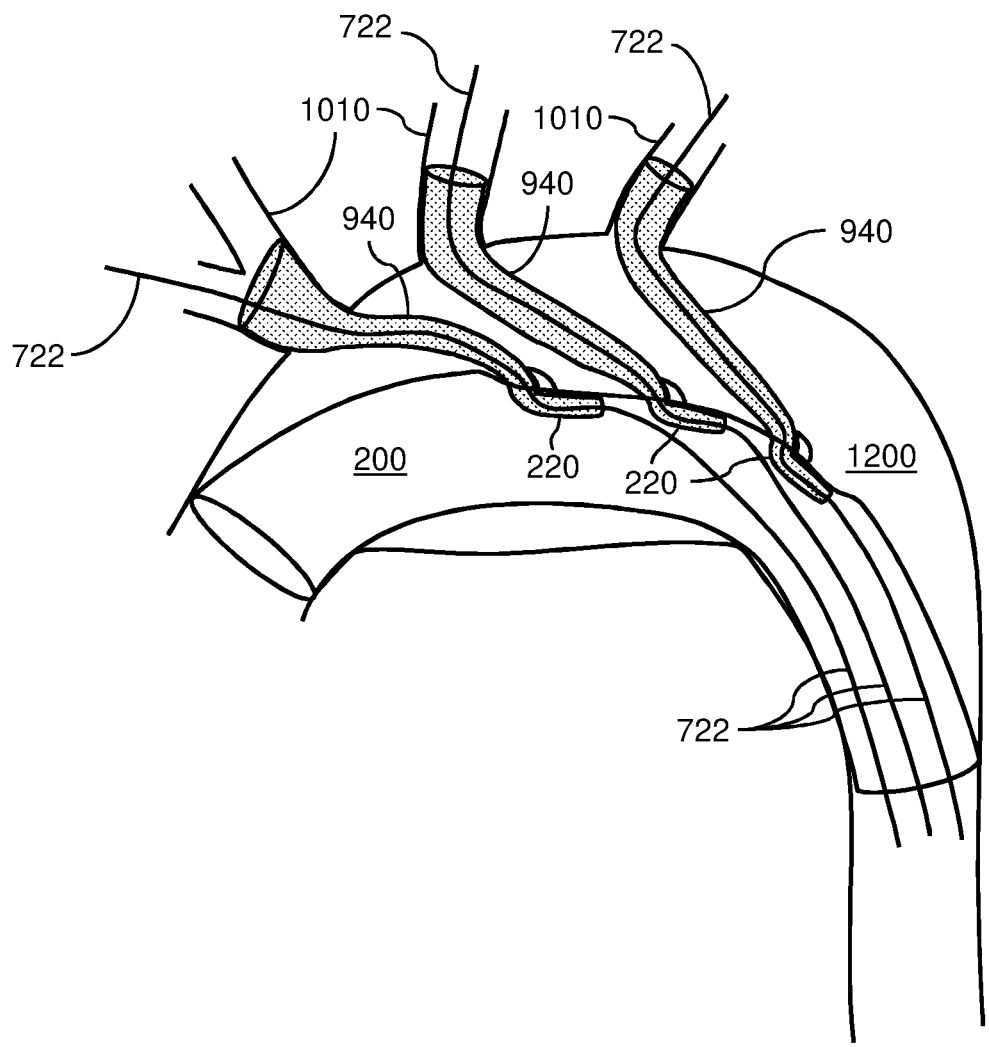
Figure 13:
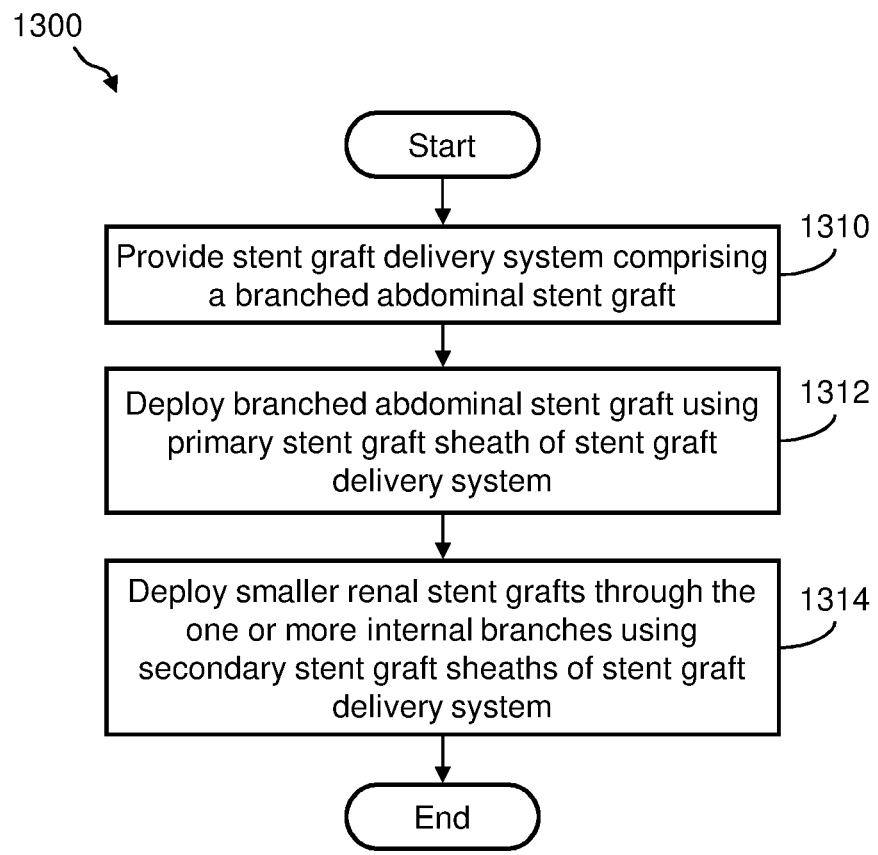
Figure 14:
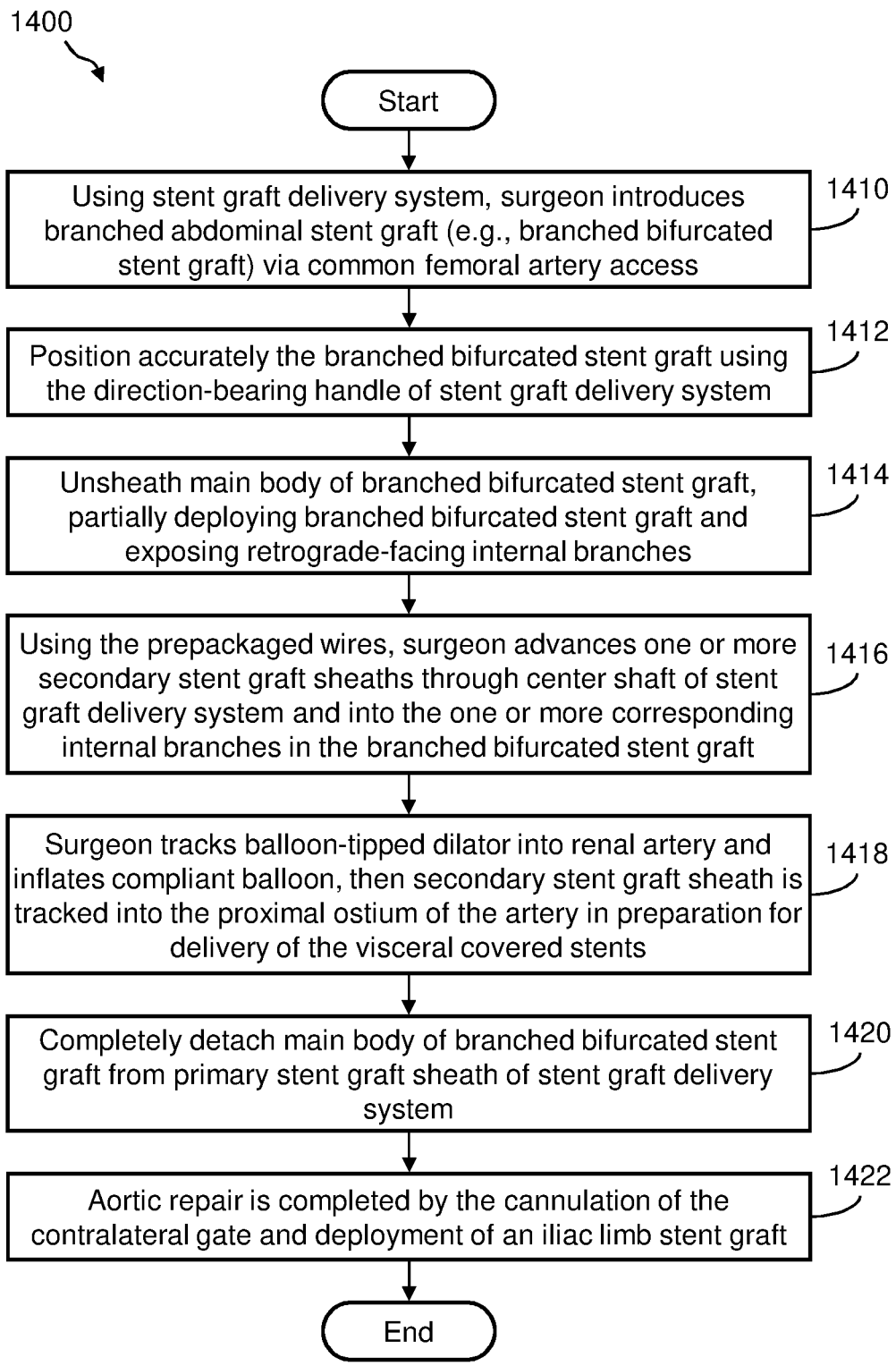
Figure 15:
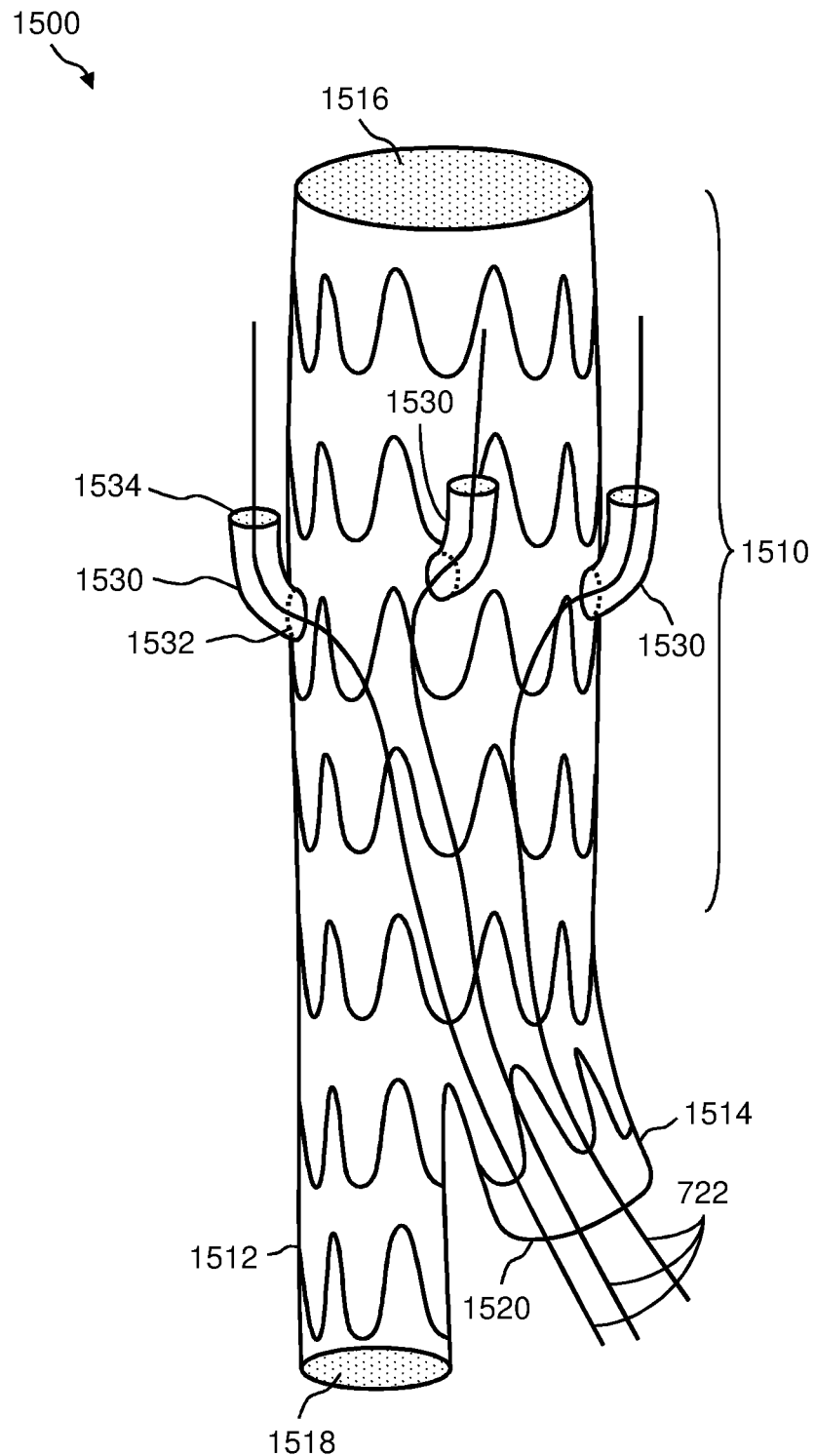
Figure 16:
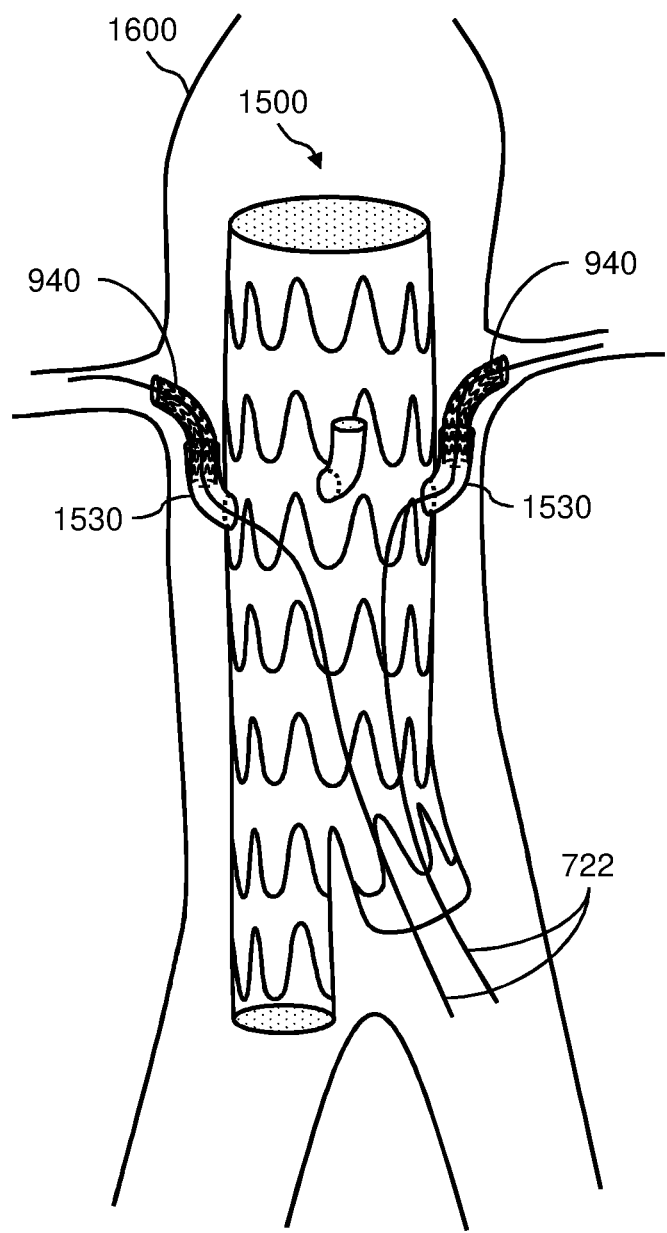

Having thus described the presently disclosed subject matter in general terms, reference will now be made to the accompanying Drawings, which are not necessarily drawn to scale, and wherein:

FIG. 1 illustrates perspective views of two examples of known abdominal stent grafts (Prior Art);

FIG. 2 illustrates a perspective front view and a perspective side view of a branched aorto-uni-iliac (AUI) stent graft, which is one example of the presently disclosed branched abdominal stent grafts that comprise one or more internal branches;

FIG. 3 shows more details of the internal branch of the presently disclosed branched abdominal stent grafts;

FIG. 4 illustrates a top down view of the distal end of the AUI stent graft shown in FIG. 2 and shows an example of an internal branch;

FIG. 5 illustrates a side view of the distal end of the branched bifurcated stent graft shown in FIG. 2 and shows an example of a fenestration for mating to the internal branch;

FIG. 6 illustrates a perspective front view and a perspective side view of a branched bifurcated stent graft, which is another example of the presently disclosed branched abdominal stent grafts that comprise one or more internal branches;

FIG. 7 illustrates a side view of an example of the presently disclosed stent graft delivery system for deploying the presently disclosed branched abdominal stent grafts for the endovascular repair of abdominal and/or thoracic aortic aneurysms;

FIG. 8 illustrates a side view of the stent graft delivery system shown in FIG. 7 that further comprises a steering mechanism;

FIG. 9 illustrates a side view of an example of the branched bifurcated stent graft that comprises three internal branches;

FIG. 10 illustrates perspective views of a thoracic stent graft and an example of an internal branch that conforms to the profile of the main body thereof;

FIG. 11 illustrates various views of the thoracic stent graft of FIG. 10 that comprises multiple internal branches and showing the relation of the internal branches one to another;

FIG. 12 shows a process of using the branched bifurcated stent graft to deploy stent grafts into the arch branches of the proximal thoracic aorta;

FIG. 13 illustrates a flow diagram of an example of a method of using the presently disclosed stent graft delivery system, according to a minimum configuration of the disclosure;

FIG. 14 illustrates a flow diagram of an example of a method of using the presently disclosed stent graft delivery system for deploying the presently disclosed branched abdominal stent grafts for the endovascular repair of abdominal and/or thoracic aortic aneurysms;

FIG. 15 illustrates a perspective view of an example of a branched bifurcated stent graft that comprises one or more external branches; and FIG. 16 shows the branched bifurcated stent graft of FIG. 15 when deployed.

DETAILED DESCRIPTION

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides branched stent grafts and a stent graft delivery system for, and methods of, endovascular repair of aortic aneurysms including abdominal and thoracic aortic aneurysms. Embodiments of the branched stent grafts include, but are not limited to, branched aorto-uni-iliac (AUI) stent grafts, branched bifurcated stent grafts, and branched thoracic stent grafts.

The presently disclosed branched stent grafts and stent graft delivery system and methods enable the surgeon to deliver a stent graft to exclude a juxtarenal/pararenal abdominal aortic aneurysm deemed appropriate for treatment by the treating physician. Features of the stent graft delivery system include, for example, (1) a multi-functional sheath through which the branched stent grafts can be delivered into the correct anatomic position, (2) bendability via a steering mechanism at the handle that aids with precise positioning, and (3) the capacity to deliver one or more smaller sheaths for the cannulation of renal arteries and the subsequent delivery of covered stents.

In some embodiments, the branched stent grafts comprise one or more retrograde internal branches. The internal branches are flared with a larger diameter as they meet the main body of the branched stent graft to provide greater freedom to select renal arteries of a variety of anatomic configurations. The retrograde-facing branches are prewired to enable expedient cannulation of arteries.

In other embodiments, the branched stent grafts comprise one or more external branches. Likewise, the external branches are prewired to enable expedient cannulation of arteries.

The stent graft delivery system comprises a larger directional sheath for positioning the branched stent grafts and one or more smaller sheaths for the delivery of covered stents for the complete exclusion of juxtarenal/pararenal abdominal aortic aneurysms. Each of these smaller sheaths (i.e., 7 French) consists of a dilator tip which is a shaped 5 to 8 millimeter compliant balloon that, when inflated, assists with the tracking and deliverability of covered stents into the renal artery. Additionally, these smaller sheaths are delivered via a larger stent graft sheath (i.e., 18 to 20 French).

The presently disclosed stent graft delivery system and methods provide a means to deliver a branched stent graft that has internal retrograde branches or external branches, which are prewired for the expedient cannulation and delivery of covered stents to one or more arteries, thereby creating a reliable proximal seal for the exclusion of juxtarenal/pararenal abdominal aortic aneurysms. The directional sheath of the main body of the branched stent graft affords accurate stent graft delivery due to its capacity to conform to the tortuosity of the native aortic neck via a control handle at the base of the sheath, a characteristic not currently a property of stent grafts currently available. Over the wires that already cannulate the retrograde internal branches (i.e., prewired) or external branches, the smaller sheaths with compliant balloon dilator tips are introduced through the stent graft sheath via a silicone ring also located at its base. Therefore, using the presently disclosed stent graft delivery system and methods for the endovascular repair of a juxtarenal/pararenal abdominal aortic aneurysm, the branched stent grafts may be delivered through single femoral access, also not currently available in the current United States market.

FIG. 1 shows perspective views of two examples of conventional abdominal stent grafts. For example, FIG. 1 shows a stent graft 100, which can be, for example, a standard tubular-shaped aorto-uni-iliac (AUI) stent graft. FIG. 1 also shows a bifurcated stent graft 110, which can be a standard bifurcated stent graft that includes, for example, a main body 112, a first limb (or leg) 114, and a second limb (or leg) 116. Namely, first limb 114 and second limb 116 extend from the proximal end of main body 112, wherein first limb 114 is longer than second limb 116 and second limb 116 is designed to receive a stent graft extension 120.

Generally, a stent graft is a synthetic fabric tube (graft) supported by a metal scaffold (stent). In these examples, stent graft 100 and bifurcated stent graft 110 are "covered" stents, meaning that stent graft 100 and bifurcated stent graft 110 are formed of tubular metal webs covered by woven polyester material.

A drawback of conventional abdominal stent grafts, such as stent graft 100 and bifurcated stent graft 110, is that they must be custom-built for each patient based on preoperative computed tomographic studies, a time-consuming and costly process. Further, anatomic features, as well as design constraints of the conventional abdominal stent grafts themselves (e.g., not placing fenestrations across device struts), limit the surgeon's capability to accurately deliver these devices.

FIG. 2 is a perspective front view and a perspective side view of a branched main body stent graft 200, which is one example of the presently disclosed branched abdominal stent grafts that comprise one or more internal branches. In this example, branched main body stent graft 200 comprises a main body 210. Main body 210 is a flexible tubular-shaped stent, which is a tubular metal web covered by a woven polyester sleeve. Accordingly, branched main body stent graft 200 is a covered stent. Main body 210 of branched AUI stent graft 200 has a distal end 212 and a proximal end 214. Branched main body stent graft 200 comprises at least one internal branch 220 inside main body 210. In the example shown in FIG. 2, branched main body stent graft 200 comprises two internal branches 220. However, this is exemplary only. Branched main body stent graft 200 can comprise any number of internal branches 220.

Each of the internal branches 220 is a flexible tubular-shaped member constructed, for example, of a nitinol skeleton covered with an expanded polytetrafluoroethylene covered stent. A distal end 222 of internal branch 220 is mated to or otherwise coupled to a fenestration or opening (see FIG. 4 and FIG. 5) in the wall of main body 210 of branched main body stent graft 200. A proximal end 224 of internal branch 220 is free hanging inside main body 210.

Each of the internal branches 220 is tapered from distal end 222 to proximal end 224. Namely, distal end 222 has a larger diameter than proximal end 224. That is, distal end 222 is a flared end of internal branch 220. For example, FIG. 3 shows more details of an internal branch 220 of the presently disclosed branched abdominal stent grafts, such as branched main body stent graft 200. Internal branch 220 has an overall length L. Distal end 222 of internal branch 220 has a diameter d1 and proximal end 224 has a diameter d2. In one example, the length L of internal branch 120 can be from about 40 mm to about 50 mm. To achieve the taper, the diameter d1 of distal end 222 can be about twice the diameter d2 of proximal end 224. In one example, the diameter d1 of distal end 222 is from 10 mm to about 12 mm, while the diameter d2 of proximal end 224 is from about 5 mm to about 6 mm. Each internal branch 220 can be marked, for example, with a gold marker in the form of a "P" (not shown) to aid with accurate positioning of the internal branch 220 in relation to the target visceral artery.

FIG. 4 and FIG. 5 are a top down view and side view, respectively, of distal end 222 of branched main body stent graft 200 shown in FIG. 2 and shows yet more details of an example of internal branch 220. In particular, FIG. 4 and FIG. 5 shows distal end 222 of internal branch 220 mated to or otherwise coupled to a fenestration or opening 230 in the wall of main body 210 of branched main body stent graft 200. For example, distal end 222 of internal branch 220 is aligned with fenestration or opening 230 and then sutured, woven, or adhered to the wall of main body 210 in the area around fenestration or opening 230.

FIG. 2 additionally shows a guide wire 250 of an endoscopy system (not shown) can run through main body 210 of branched main body stent graft 200. Namely, guide wire 250 enters proximal end 214 and exits distal end 212 of main body 210. In similar fashion, another guide wire 255 of an endoscopy system (not shown) can run through internal branch 220 inside main body 210 of branched main body stent graft 200. Namely, guide wire 255 enters proximal end 224 and exits distal end 222 of internal branch 220. Guide wire 250 running through main body 210 can be a larger diameter wire than guide wire 255 running through internal branch 220. For example, guide wire 250 can be the guide wire in an 18 to 20 French stent graft sheath, while guide wire 255 can be the guide wire in a 7 French stent graft sheath.

FIG. 6 shows a perspective front view and a perspective side view of a branched bifurcated stent graft 600, which is another example of the presently disclosed branched abdominal stent grafts that comprise one or more internal branches. Namely, branched bifurcated stent graft 600 is a bifurcated stent graft that comprises one or more internal branches 220.

In this example, branched bifurcated stent graft 600 includes a main body 610, a first limb (or leg) 612, and a second limb (or leg) 614. Namely, first limb 612 and second limb 614 extend from the proximal end of main body 610, wherein first limb 612 is longer than second limb 614 and second limb 614 is designed to receive a stent graft extension (not shown). Namely, a stent graft extension (e.g., proximal extension thoracic stent graft, not shown) is provided with branched bifurcated stent graft 600 for connecting to second limb 614.

Main body 610, first limb 612, and second limb 614 are flexible tubular-shaped members, each of which is a tubular metal web covered by a woven polyester sleeve. Accordingly, branched bifurcated stent graft 600 is a covered stent. Main body 610 has a distal end 616. First limb 612 has a proximal end 618. Second limb 614 has a proximal end 620.

Branched bifurcated stent graft 600 comprises at least one internal branch 220 inside main body 610, wherein internal branch 220 is the internal branch described with reference to branched main body stent graft 200 shown in FIG. 2 through FIG. 5. In the example shown in FIG. 6, branched bifurcated stent graft 600 comprises one internal branch 220. However, this is exemplary only. Branched bifurcated stent graft 600 can comprise any number of internal branches 220.

The use of branched AUI stent graft 200 and/or branched bifurcated stent graft 600 can be briefly summarized as follows. First, branched AUI stent graft 200 and/or branched bifurcated stent graft 600 is deployed from the groin into, for example, the proximal descending thoracic aorta. Then, the one or more internal branches 220 are used to deploy smaller renal stent grafts (not shown) from the groin into the arch branches of the thoracic aorta (see FIG. 12). For example, using an internal branch 220, the renal artery can be cannulated first with a guide wire, then a small stent graft sheath, and then a small renal stent graft.

A stent graft delivery system for deploying the presently disclosed branched abdominal stent grafts, such as branched AUI stent graft 200 and branched bifurcated stent graft 600, is described herein below with reference to FIG. 7 and FIG. 8.

FIG. 7 shows a side view of an example of the presently disclosed stent graft delivery system 700 for deploying the presently disclosed branched abdominal stent grafts, such as branched AUI stent graft 200 and branched bifurcated stent graft 600, for the endovascular repair of abdominal and/or thoracic aortic aneurysms.

Stent graft delivery system 700 comprises a primary stent graft sheath 710. Primary stent graft sheath 710 is the directional mechanism of stent graft delivery system 700.

A guide wire 712 runs through primary stent graft sheath 710. A top cap 714 is at the distal end of guide wire 712. Top cap 714 is, for example, a bullet-shaped plastic cap. Primary stent graft sheath 710 is the directional sheath and largest sheath of stent graft delivery system 700. Primary stent graft sheath 710 can be, for example, an 18 to 20 French stent graft sheath. In one example, primary stent graft sheath 710 is constructed of nitinol-reinforced hydrophilic pliable plastic measuring about 50 cm long and delivered over any commercially available 0.035" wire, which is guide wire 712.

Primary stent graft sheath 710 encompasses a center shaft 716 through which other smaller sheaths may be introduced (e.g., stent graft sheaths 720). Center shaft 716 is a length of hollow flexible tubing, such as plastic or silicone tubing. In one example, the diameter of center shaft 716 is about 9.0 millimeters. One or more openings 718 are provided in the sides of center shaft 716 and near the distal end thereof.

Branched AUI stent graft 200 or branched bifurcated stent graft 600 is provided in relation to primary stent graft sheath 710 and center shaft 716. For example, FIG. 7 shows primary stent graft sheath 710 running through center shaft 716 and then through first limb 612 and main body 610 of branched bifurcated stent graft 600. In this example, branched bifurcated stent graft 600 comprises two internal branches 220. Primary stent graft sheath 710 may be sutured to the inner wall of branched bifurcated stent graft 600.

In this example, because branched bifurcated stent graft 600 comprises two internal branches 220, stent graft delivery system 700 further comprises two secondary stent graft sheaths 720 (e.g., secondary stent graft sheaths 720a, 720b). Each of the secondary stent graft sheaths 720 is used for visceral artery covered stent delivery. Secondary stent graft sheaths 720 are small sheaths compared to primary stent graft sheath 710. Secondary stent graft sheaths 720 can be, for example, 7 French stent graft sheaths constructed of hydrophiliac pliable plastic and measuring about 50 cm in length and reinforced with a nitinol skeleton.

Each of the secondary stent graft sheaths 720 has a guide wire 722 running therethrough. For example, a guide wire 722a for secondary stent graft sheath 720a and a guide wire 722b for secondary stent graft sheath 720b. The diameter of guide wire 722 can be, for example, about 0.035 inches or about 0.018 inches. Further, each of the secondary stent graft sheaths 720 may contain a 5 to 8 French compliant balloon dilator tip for the delivery of renal artery covered stents. In one example, the balloon dilator tip comprises a pre-formed 5-8 mm balloon (not shown) that is about 3-4 cm long, wherein the balloon may be guided into the aortic arch branch. The balloon may add stability to the system when delivering the renal stent grafts. This dilator may be advanced distal to the sheath itself to enable the inflated balloon located within a visceral artery to act as an anchor for the advancement of the sheath within the arterial ostium. The balloon can then be deflated and removed over the wire, leaving the sheath in its desired location. This component promotes trackability of the sheath into a visceral vessel in difficult anatomic scenarios as well as reduces the number of catheter/sheath exchanges, contributing to the efficiency of the overall operation.

Further, each of the secondary stent graft sheaths 720 has a standard hemostatic valve 724 at the proximal end thereof. For example, a hemostatic valve 724a for secondary stent graft sheath 720a and a hemostatic valve 724b for secondary stent graft sheath 720b.

In this example, secondary stent graft sheath 720a and guide wire 722a enter the proximal end of center shaft 716. Secondary stent graft sheath 720a and guide wire 722a run through center shaft 716 and then exit the side of center shaft 716 via one of the openings 718. Then, secondary stent graft sheath 720a and guide wire 722a enter the proximal end of second limb 614 of branched bifurcated stent graft 600. Secondary stent graft sheath 720a and guide wire 722a run through second limb 614 of branched bifurcated stent graft 600 and then enter proximal end 224 of the first internal branch 220. Then, secondary stent graft sheath 720a and guide wire 722a exit the distal end 222 of the first internal branch 220 and exit the side of branched bifurcated stent graft 600 via its corresponding fenestration or opening 230.

In like manner, secondary stent graft sheath 720b and guide wire 722b enter the proximal end of center shaft 716. Secondary stent graft sheath 720b and guide wire 722b run through center shaft 716 and then exit the side of center shaft 716 via one of the openings 718. Secondary stent graft sheath 720b and guide wire 722b then enter the proximal end of first limb 612 of branched bifurcated stent graft 600. Secondary stent graft sheath 720b and guide wire 722b run through first limb 612 of branched bifurcated stent graft 600 and then enter proximal end 224 of the second internal branch 220. Then, secondary stent graft sheath 720b and guide wire 722b exit the distal end 222 of the second internal branch 220 and exit the side of branched bifurcated stent graft 600 via its corresponding fenestration or opening 230.

Referring now to FIG. 8 shows a side view of stent graft delivery system 700 shown in FIG. 7 that further comprises a steering mechanism. For example, the steering mechanism comprises a handle 730 and two strings 732. One end of the pair of strings 732 is coupled to handle 730. The pair of strings 732 are integrated into primary stent graft sheath 710. The opposite end of the pair of strings 732 is coupled to the distal end of primary stent graft sheath 710. Namely, about 5 cm centimeters from the distal end of the inner shaft of primary stent graft sheath 710, two 0.018" strings (e.g., two strings 732) attach at the three and nine o'clock positions and travel along the inner shaft through the outer sheath and attach at the same positions to a two inch-long handle 730. According to one non-limiting aspect of the present disclosure, for example, with clockwise revolution of the hand, the stent graft and distal inner shaft of stent graft delivery system 700 tilts to the left; with counter-clockwise revolution, the stent graft and distal inner shaft of stent graft delivery system 700 tilt to the right.

Further, a pull control 734 may be provided on center shaft 716 to unwrap branched bifurcated stent graft 600.

In one embodiment, a silicone ring (not shown) may be provided just below pull control 734 and proximal to handle 730. Catheters and sheaths may be introduced through this ring wherein the silicone keeps the sheaths hemostatic as it seals around them. Sheaths and catheters that pass through the silicone ring enter the main common channel of the stent graft delivery system 700.

According to an aspect of the present disclosure, the operation of stent graft delivery system 700 can be briefly summarized as follows. First, primary stent graft sheath 710 is used to deploy the presently disclosed branched abdominal stent grafts, such as branched main body stent graft 200 (FIG. 2) and/or branched bifurcated stent graft 600, into and from the groin, then into, for example, the proximal descending thoracic aorta or juxtarenal abdominal aorta. Then, the secondary stent graft sheaths 720 are used to deploy smaller renal stent grafts (not shown) to and through the one or more internal branches 220 and then into the arch branches of the thoracic aorta (see FIG. 12). For example, using an internal branch 220, the renal artery can be cannulated first with guide wire 722, then the small secondary stent graft sheath 720, and then the small renal stent graft (not shown). The flared distal end 222 of the internal branches 220 assists in the selectivity of the aortic arch branches. For example, the flared distal end 222 of the internal branches 220 provides greater freedom to select renal arteries of a variety of anatomic configurations as compared with conventional stent graft delivery systems.

According to an aspect of the present disclosure, stent graft delivery system 700 is provided as a kit packaged with branched main body stent graft 200 or branched bifurcated stent graft 600 and with the one or more internal branches 220 of branched main body stent graft 200 or branched bifurcated stent graft 600 prewired with secondary stent graft sheaths 720. For example, FIG. 9 shows a side view of an example of branched AUI stent graft 200 that comprises three internal branches 220, which are prewired with three respective guide wires 722. FIG. 9 also shows that the side of branched main body stent graft 200 that has the three internal branches 220 may be contoured (e.g., contoured portion 226). Contoured portion 226 is provided to assist with packing the branched main body stent graft 200 and to assist arch vessel selection using catheter manipulation. Further, FIG. 9 shows that branched main body stent graft 200 may include a barb 228 on the side of main body 210 at each internal branch 220. Barbs 228 can be flaps of fabric that help form a seal between the small renal stent grafts and branched main body stent graft 200. In similar fashion, branched bifurcated stent graft 600 may include a contoured portion and barbs.

The use of "branches" is not limited to abdominal stent grafts (e.g., bifurcated stent grafts and AUI stent grafts), rather the use of "branches" can be also extended to thoracic components, such as thoracic stent graphs. More details of examples of thoracic stent graphs that include branches are described hereinbelow with reference to FIG. 10 and FIG. 11.

FIG. 10 shows perspective views of a branched thoracic stent graft 900 and an example of an internal branch 930 that substantially conforms to the profile of the main body thereof. For example, branched thoracic stent graft 900 includes a main body 910 (e.g., a tubular body) that has a proximal end 912 and a distal end 914. In this example, internal branch 930 runs in the same direction as main body 910 and is maintained in a substantially fixed position just under the surface of main body 910. Internal branch 930 has a proximal end 932 and a distal end 934. Proximal end 932 is accessible from inside main body 910, while distal end 934 is configured to emerge from main body 910 within a contoured portion 916 thereof. When in use, a smaller stent graft (or bridging stent graft) 940 can be deployed from internal branch 930.

In one example, internal branch 930 has a diameter of from about 8 mm to about 10 mm. Accordingly, the depth of contoured portion 916 can also be from about 8 mm to about 10 mm in diameter. Further, the portion at proximal end 912 of main body 910 that is outside contoured portion 916 can be a proximal seal zone 918. In one example, proximal seal zone 918 is about 30 mm long. The portion at distal end 914 of main body 910 that is outside contoured portion 916 can be a distal seal zone 920. In one example, distal seal zone 920 is about 20 mm long. However, the seal zones can generally range from about 15 cm to about 30 cm.

FIG. 11 shows a side view, top view, and end view of an example of branched thoracic stent graft 900 that comprises multiple internal branches 930a, 930b, 930c and showing the relation of the internal branches 930a, 930b, 930c one to another. In this example, branched thoracic stent graft 900 includes three internal branches 930a, 930b, 930c. Branched thoracic stent graft 900 can be prewired and deployed using, for example, stent graft delivery system 700 (see FIG. 7 and FIG. 8).

The end view (proximal end) of branched thoracic stent graft 900 shows the predetermined spacing/positions of internal branches 930a, 930b, 930c around the circumference of main body 910, while the side and top views are intended to show an exemplary staggered relation of the internal branches 930a, 930b, 930c. For example, in the end view, if internal branch 930b is at 12 o'clock, then internal branch 930c is at about 10 o'clock, and internal branch 930a is at about 2 o'clock.

According to one aspect, as shown, the distal ends of internal branches 930a, 930b, 930c all emerge from contoured portion 916 of main body 910. In this example, internal branch 930a is a certain length, internal branch 930b is a slightly shorter length than internal branch 930a, and internal branch 930c is a slightly shorter length than internal branch 930c. In one example, the overall length of main body 910 of branched thoracic stent graft 900 can be from about 12 cm to about 20 cm.

As shown in FIG. 11, branched thoracic stent graft 900 is a partially constrained main body thoracic stent graft with internal branches 930a, 930b, 930c that are arranged in a predetermined staggered fashion within this constrained portion (e.g., within contoured portion 916). This enables a lower profile device with less graft material required to be packaged, thereby increasing the ability of the surgeon to deliver the stent graft with fewer access site complications. Positioning internal branches 930a, 930b, 930c within the constrained portion (e.g., within contoured portion 916) of main body 910, enables more room within the blood vessel to cannulate or select the main branches that come off the aorta that are being preserved with the bridging stent grafts (e.g., bridging stent grafts 940).

FIG. 12 is a side view showing a process of using branched main body stent graft 200 of FIG. 2, wherein three bridging stent grafts 940 are fully deployed to predetermined locations into the three thoracic aortic branches 1010 of the proximal descending thoracic aorta 1200 by use of branched main body stent graft 200. In FIG. 12, whereas the larger primary stent graft sheath 710 is used to deploy branched main body stent graft 200, the smaller secondary stent graft sheaths 720 are used to deploy the bridging stent grafts 940 through the internal branches 220.

FIG. 13 is a flow diagram of an example of a method of using the presently disclosed stent graft delivery system 700 to deploy the presently disclosed branched stent grafts, according to a minimum configuration of the disclosure. Method 1300 may include, but is not limited to, the following steps.

At a step 1310, stent graft delivery system 700 that includes a certain type of branched abdominal stent graft is provided. In one example, stent graft delivery system 700 is packaged with a branched main body stent graft 200 and provided to the surgeon. In another example, stent graft delivery system 700 is packaged with a branched bifurcated stent graft 600 and provided to the surgeon. In another example, stent graft delivery system 700 is packaged with a branched thoracic stent graft 900 and provided to the surgeon.

At a step 1312, primary stent graft sheath 710 of stent graft delivery system 700 is used to deploy the presently disclosed branched abdominal stent graft, such as branched main body stent graft 200, branched bifurcated stent graft 600, or branched thoracic stent graft 900 from the groin into, for example, the proximal descending thoracic aorta or juxtarenal abdominal aorta, respectively.

At a step 1314, the secondary stent graft sheaths 720 are used to deploy smaller renal stent grafts to and through the one or more internal branches 220 and then into the arch branches of the thoracic aorta (see FIG. 12). For example, using an internal branch 220, the renal artery can be cannulated first with guide wire 722, then the small secondary stent graft sheath 720, and then the small renal stent graft (not shown). The flared distal end 222 of the internal branches 220 assists in the selectivity of the aortic arch branches. Further, in the case of branched bifurcated stent graft 600, the stent graft extension (e.g., proximal extension thoracic stent graft, not shown) is deployed and connected to second limb 614.

FIG. 14 is a flow diagram of an example of a method 1400 of using the presently disclosed stent graft delivery system 700 for deploying the presently disclosed branched stent grafts for the endovascular repair of abdominal and/or thoracic aortic aneurysms. By way of example, branched bifurcated stent graft 600 of FIG. 6 is deployed using method 1400. Method 1400 may include, but is not limited to, the following steps.

At a step 1410, using primary stent graft sheath 710 of stent graft delivery system 700, the surgeon introduces branched bifurcated stent graft 600 via the common femoral artery access, either percutaneously or via open arterial exposure.

At a step 1412, branched bifurcated stent graft 600 is positioned accurately to a predetermined location using the direction-bearing handle 730, based upon the tortuosity of the native aorta at the level of the superior mesenteric artery and one or both renal arteries, which is determined either by preoperative mapping based upon computed tomographic angiography imaging and/or aortography. Handle 730 translates movement from the surgeon into precise and predetermined movements of primary stent graft sheath 710 at the level of the branched abdominal stent graft (e.g., branched bifurcated stent graft 600).

At a step 1414, main body 610 of branched bifurcated stent graft 600 is unsheathed, partially deploying branched bifurcated stent graft 600 and exposing the retrograde-facing internal branches 220 that will be used to assist with preservation of renal artery perfusion.

At a step 1416, over the exemplary 0.018" guide wire 722 that, according to one aspect of the disclosure are prepackaged with stent graft delivery system 700 and exiting though center shaft 716 located proximal to the directional handle 730, the surgeon advances the one or more secondary stent graft sheaths 720 having a balloon dilator up through center shaft 716 into the one or more corresponding internal branches 220. The flared ends of internal branches 220 provides the surgeon enough working room to cannulate each renal artery, either with the prepackaged wire 722 and balloon tip dilator or a commercially available catheter followed by the secondary stent graft sheath 720.

At a step 1418, once the surgeon tracks the balloon-tipped dilator into the renal artery and inflates the compliant balloon, the secondary stent graft sheath 720 may be tracked into the proximal ostium of the artery in preparation for delivery of the visceral covered stents (e.g., bridging stent grafts 940 shown in FIG. 12). For example, balloon-expandable covered stent grafts (e.g., bridging stent grafts 940 shown in FIG. 12) are deployed, which bridge the native renal artery with the internal branch, thereby creating a seal that excludes blood flow from the aneurysm sac but also promotes continued visceral perfusion.

At a step 1420, main body 610 of branched bifurcated stent graft 600 is completely detached from primary stent graft sheath 710 of stent graft delivery system 700 via the removal of a constraining wire that is located along the posterior spine of branched main body stent graft 200 or branched bifurcated stent graft 600. This is accomplished by the removal of a plug (not shown) that is attached to this constraining wire that is located just proximal to center shaft 716.

At a step 1422, the completion of the aortic repair consists of cannulation of the contralateral gate and deployment of an iliac limb stent graft (e.g., stent graft extension or proximal extension thoracic stent graft) consistent with currently marketed stent graft devices. The common femoral arteriotomy is then closed as per currently accepted methods.

FIG. 15 is a perspective view of an example of a branched bifurcated stent graft 1500 that comprises one or more external branches. In this example, branched bifurcated stent graft 1500 includes a main body 1510, a first limb (or leg) 1512, and a second limb (or leg) 1514. Namely, first limb 1512 and second limb 1514 extend from the proximal end of main body 1510, wherein first limb 1512 is longer than second limb 1514 and second limb 1514 is designed to receive a stent graft extension (not shown).

Main body 1510, first limb 1512, and second limb 1514 are flexible tubular-shaped members, each of which is a tubular metal web covered by a woven polyester sleeve. Accordingly, branched bifurcated stent graft 1500 is a covered stent. Main body 1510 has a distal end 1516. First limb 1512 has a proximal end 1518. Second limb 1514 has a proximal end 1520.

Branched bifurcated stent graft 1500 comprises at least one external branch 1530 that protrudes from the side of main body 1510. In the example shown in FIG. 15, branched bifurcated stent graft 1500 comprises three external branches 1530. However, this is exemplary only. Branched bifurcated stent graft 1500 can comprise any number of external branches 1530. In one example, each of the external branches 1530 is about 2 cm long and is about 7 mm in diameter.

FIG. 16 shows branched bifurcated stent graft 1500 of FIG. 15 when deployed in, for example, the juxtarenal abdominal aorta 1600 and shown in relation to the renal arteries. Branched bifurcated stent graft 1500 can be prewired and deployed using, for example, stent graft delivery system 700. In this example, the one or more external branches 1530 are used to deploy smaller renal stent grafts (or bridging stent grafts) 940 into, for example, the renal arteries of the abdominal aorta.

In branched bifurcated stent graft 1500, by having the external branches 1530 protrude from the sides of main body 1510 upon deployment, the flow dynamics may be improved within main body 1510 of branched bifurcated stent graft 1500. Additionally, the branched bifurcated stent graft 1500 with the external branches 1530 may serve to decrease type II endoleaks (i.e., back bleeding from spinal arteries that feed the aneurysm sac). Further, the use of external branches 1530 is not limited to bifurcated stent grafts only, rather external branches 1530 can also be used with main body stent grafts.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the disclosed subject matter.

What is claimed is:

1. A kit comprising:
   a stent graft comprising a main body section, the main body section having an outer wall, the outer wall having an outer wall profile, the outer wall having at least one fenestration and at least one tapered internal branch in communication with the fenestration, the at least one tapered internal branch having a proximal end and a distal end, the proximal end in communication with the fenestration, and wherein the at least one tapered internal branch tapers from the proximal end to the distal end, wherein the main body section comprises a contoured portion, the contoured portion formed from an indentation in the outer wall of the main body section that extends along the main body section to at least a length configured to contain a plurality of tapered internal branches, wherein the contoured portion is located between a proximal end and a distal end of the main body section, the proximal and distal end of the main body section having substantially the same diameter, and wherein the at least one tapered internal branch is located within the contoured portion;
   a primary stent graft sheath configured to accommodate a primary guide wire passing through the primary stent graft sheath; and
   at least one secondary stent graft sheath configured to accommodate at least one secondary guide wire passing through said secondary stent graft sheath.

2. The kit of claim 1, wherein the main body is substantially cylindrical and substantially hollow.

3. The kit of claim 1, wherein the stent graft is a branched stent graft.

4. The kit of claim 1, wherein the stent graft is a branched bifurcated stent graft.

5. The kit of claim 1, wherein the stent graft is a covered stent graft.

6. The kit of claim 1, wherein the branch is substantially frustoconical in shape, with the proximal end having a proximal end opening diameter that is greater than a distal end opening diameter.

7. The kit of claim 1, wherein the branch extends inward from the outer wall of the main body and into the main body for a predetermined distance.

8. The kit of claim 1, wherein the branch extends outward from the outer wall of the main body and outside of the main body for a predetermined distance.

9. The kit of claim 1, wherein the branch substantially conforms to the outer wall profile.

10. The kit of claim 1, further comprising at least one secondary stent graft dimensioned to pass into the fenestration and into the branch that is in fixed communication with the fenestration.

11. The kit of claim 1, further comprising a sealing barb located at the at least one fenestration.

12. The kit of claim 1, wherein the contoured portion has a depth of about 8 mm to about 10 mm.

13. The kit of claim 1, wherein a plurality of internal branches emerge from within the contoured portion of the main body.

* * * * *